(12) United States Patent
Kim et al.

(10) Patent No.: US 10,894,895 B2
(45) Date of Patent: Jan. 19, 2021

(54) TWO-COMPONENT BIOINK, 3D BIOMATERIAL COMPRISING THE SAME AND METHOD FOR PREPARING THE SAME

(71) Applicant: AJOU UNIVERSITY INDUSTRY-ACADEMIC COOPERATION FOUNDATION, Suwon-si (KR)

(72) Inventors: Kyung Sook Kim, Suwon-si (KR); Da Yeon Kim, Yongin-si (KR); Seung Hun Park, Seoul (KR); Ja Yong Jang, Busan (KR); Moon Suk Kim, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 252 days.

(21) Appl. No.: 15/739,628

(22) PCT Filed: Jun. 27, 2016

(86) PCT No.: PCT/KR2016/006863
§ 371 (c)(1),
(2) Date: Dec. 22, 2017

(87) PCT Pub. No.: WO2016/209062
PCT Pub. Date: Dec. 29, 2016

(65) Prior Publication Data
US 2018/0215934 A1    Aug. 2, 2018

(30) Foreign Application Priority Data

Jun. 26, 2015    (KR) .................. 10-2015-0091435

(51) Int. Cl.
| | | |
|---|---|---|
| C09D 11/14 | (2006.01) | |
| C09D 11/30 | (2014.01) | |
| C09D 105/04 | (2006.01) | |
| C09D 11/08 | (2006.01) | |
| C09D 105/08 | (2006.01) | |
| C09D 101/28 | (2006.01) | |
| C12N 5/00 | (2006.01) | |
| A61K 47/34 | (2017.01) | |
| A61K 47/36 | (2006.01) | |
| A61K 47/38 | (2006.01) | |
| A61L 27/26 | (2006.01) | |
| A61L 27/38 | (2006.01) | |

(Continued)

(52) U.S. Cl.
CPC .............. *C09D 11/14* (2013.01); *A61K 47/34* (2013.01); *A61K 47/36* (2013.01); *A61K 47/38* (2013.01); *A61L 27/26* (2013.01); *A61L 27/3804* (2013.01); *A61L 27/3826* (2013.01); *A61L 27/3834* (2013.01); *A61L 31/041* (2013.01); *A61L 31/16* (2013.01); *C09D 11/08* (2013.01); *C09D 11/102* (2013.01); *C09D 11/30* (2013.01); *C09D 101/286* (2013.01); *C09D 105/04* (2013.01); *C09D 105/08* (2013.01); *C12N 5/0062* (2013.01); *C12N 5/0068* (2013.01); *A61L 2300/424* (2013.01)

(58) Field of Classification Search
CPC ........ A61K 47/34; A61K 47/36; A61K 47/38; A61L 2300/424; A61L 27/26; A61L 27/2804; A61L 27/3826; A61L 31/041; A61L 31/16; C09D 101/286; C09D 105/04; C09D 105/08; C09D 11/08; C09D 11/102; C09D 11/14; C09D 11/30; C12N 5/0062; C12N 5/0068
See application file for complete search history.

(56) References Cited

U.S. PATENT DOCUMENTS

| | | | | |
|---|---|---|---|---|
| 2004/0086493 | A1* | 5/2004 | Hubbell | .............. C08B 37/0084 424/93.7 |
| 2011/0033543 | A1* | 2/2011 | Kiick | .................. A61K 9/1641 424/484 |

(Continued)

FOREIGN PATENT DOCUMENTS

| | | | |
|---|---|---|---|
| EP | 2 789 685 A1 | 10/2014 | |
| KR | 10-2010-0128565 A | 12/2010 | |

(Continued)

OTHER PUBLICATIONS

Chung et al. Biomaterials (2002) 23: 2834 (Year: 2002).*

(Continued)

*Primary Examiner* — Susan M Hanley
(74) *Attorney, Agent, or Firm* — Vorys, Sater, Seymour & Pease LLP; Mih Suhn Koh

(57) ABSTRACT

The present invention provides a two-component bioink including a first solution and a second solution separately, wherein (i) the first solution includes a first biopolymer to which a first chemical functional group is introduced, and the second solution includes a second biopolymer to which a second chemical functional group able to chemically bond with the first chemical functional group is introduced; or (ii) the first solution includes a third biopolymer having a first electrostatic functional group, and the second solution includes a fourth biopolymer having a second electrostatic functional group able to physically bond with the first electrostatic functional group, a 3D biomaterial including the same, and a method for preparing the same.

8 Claims, 18 Drawing Sheets

(51) Int. Cl.
*A61L 31/04* (2006.01)
*A61L 31/16* (2006.01)
*C09D 11/102* (2014.01)

(56) References Cited

U.S. PATENT DOCUMENTS

2011/0076665 A1    3/2011   Gatenholm et al.
2012/0149781 A1*   6/2012   Lee .................. C12N 5/0618
                                                 514/773

FOREIGN PATENT DOCUMENTS

| KR | 10-2013-0042857 A | 4/2013 |
| WO | 2014/085725 A1 | 6/2014 |
| WO | 2015/038914 A1 | 3/2015 |

OTHER PUBLICATIONS

Hiemstra et al. Biomacromolecules (2007) 8: 1548-1556 (Year: 2007).*
Madl et al. Adv. Functional Materials (Jun. 7, 2016) 26(21): 3612-3620 (Year: 2016).*
Yang et al. Progress in Polymer Science (2014) 39: 1973-1986 (Year: 2014).*
Zhang et al. ACS Macro Letters (2014) 3: 727-731 (Year: 2014).*
Crescenzi et al. Biomacromolecules (2007) 8: 1844-1850 (Year: 2007).*
Cengiz et al. Chem. Comm. (2013) 49: 11191-11193 (Year: 2013).*
Hamid et al. Biomaterials (2010) 31: 6454-6467 (Year: 2010).*
Skardal et al., "Photocrosslinkable Hyaluronan-Gelatin Hydrogels for Two-Step Bioprinting", Tissue Engineering: Part A, vol. 16, No. 8, pp. 2675-2685, (2010).
Kirchmajer et al., "An overview of the suitability of hydrogel-forming polymers for extrusion-based 3D-printing", J. Mater. Chem. B., vol. 3, pp. 4105-4117, (2015).

* cited by examiner (a)

(b)

TWO-COMPONENT BIOINK, 3D BIOMATERIAL COMPRISING THE SAME AND METHOD FOR PREPARING THE SAME

TECHNICAL FIELD

The present invention relates to a two-component bioink, a 3D biomaterial including the same and a method for preparing the same.

BACKGROUND ART

Due to an increase of aging population, imbalance between supply and demand of organs is emerging, even as a social problem. As years go by, the waiting list for organ transplant is growing, but the number of organ donors is at a standstill. As a fundamental solution for such a problem, tissue engineering enabling tissue and organ regeneration is being spotlighted.

Of the three main elements (cells, a scaffold and a bioactive molecule) constituting tissue engineering, for a scaffold, selection of components and structural control technology are very important. That is, the scaffold serves as a bridge connecting tissue parts to regenerate damaged tissue by a self-recovery function, and to this end, the scaffold must be cytotropic to facilitate tissue regeneration. Also, the scaffold needs to be a porous structure with pores in a predetermined size range that are three-dimensionally well linked to facilitate three-dimensional cell growth, exchange nutrients and excretions, and have biodegradation according to tissue regeneration rate, mechanical strength to keep a shape during regeneration, and excellent biological safety. Particularly, for regeneration of hard tissue such as bones and teeth, it is important to ensure a mechanical property depending on the regenerated part.

Specifically, a scaffold for tissue regeneration should (1) be physically stable at an implant part, (2) have physiological activity for regulating regeneration efficiency, and (3) be degraded in vivo after new tissue is generated, and (4) have a non-toxic degradation product.

As a conventional method for preparing a scaffold, salt leaching, particle leaching, gas foaming or electrospinning may be used, and such a method has a difficulty in controlling porosity and the shape of a scaffold during manufacturing. Therefore, bioprinting technology which is a concept of printing tissue/organ customized for a patient is attracting the attention of many people. However, due to a lack of a biomaterial for printing having the above-described requirements for a scaffold including physical stability, regulation of a bioactive factor, biodegradability and biocompatibility, there is a limit to the application of the bioprinting technology.

PRIOR ART (Patent Document 1) Korean Patent No. 10-0947290

DISCLOSURE

Technical Problem

The present invention is directed to providing a two-component bioink that can solve the problems of the conventional art and is biocompatible, a 3D biomaterial including the same, and a method for preparing the same.

Also, by adding cells, a material for preventing adhesion, a dye or a drug to the two-component bioink, the resulting bioink may be applied to various 3D biomaterial fields such as a tissue-engineered scaffold, a drug carrier or an anti-adhesive agent.

Technical Solution

The present invention provides a two-component bioink, including a first solution and a second solution separately, wherein (i) the first solution includes a first biopolymer to which a first chemical functional group is introduced, and the second solution includes a second biopolymer to which a second chemical functional group able to chemically bond with the first chemical functional group is introduced; or (ii) the first solution includes a third biopolymer having a first electrostatic functional group, and the second solution includes a fourth biopolymer having a second electrostatic functional group able to physically bond with the first electrostatic functional group.

In an exemplary embodiment of the present invention, a two-component cartridge for a 3D printer containing the two-component bioink is provided.

In another exemplary embodiment of the present invention, a 3D biomaterial prepared by chemically or physically combining the two-component bioink is provided.

In still another exemplary embodiment of the present invention, a method for preparing a 3D biomaterial, which includes: (a-1) preparing a first solution by adding a material having a first chemical functional group to a first biopolymer; (b-1) preparing a second solution by adding a material having a second chemical functional group able to chemically bond with a first chemical functional group to a second biopolymer; and (c-1) chemically combining the first solution with the second solution, or (a-2) preparing a first solution having a third biopolymer having a first electrostatic functional group; (b-2) preparing a second solution having a fourth biopolymer having a second electrostatic functional group; and (c-2) physically combining the first solution with the second solution.

Advantageous Effects

Since two-component bioinks according to various exemplary embodiments of the present invention that are biocompatible liquid compositions having a chemical or physical combination due to an electrostatic attraction are applied to a 3D printer, an excellent effect is exhibited for providing a solid 3D biomaterial.

Also, as cells, a material for preventing adhesion, a dye or a drug is added to the two-component bioink, the resulting bioink can be applied to various fields including 3D biomaterial fields such as a tissue-engineered scaffold, a drug carrier or an anti-adhesive agent.

DESCRIPTION OF DRAWINGS

FIG. 11(a) shows a tissue-engineered scaffold printed with the two-component bioink of Example 36, FIG. 11(b) shows a tissue-engineered scaffold printed with the two-component bioink of Example 37, FIG. 11(c) shows a scaffold printed with the two-component bioink of Example 38, and FIG. 11(d) shows a scaffold printed with the two-component bioink of Example 39.

BEST MODE

Figure 1:
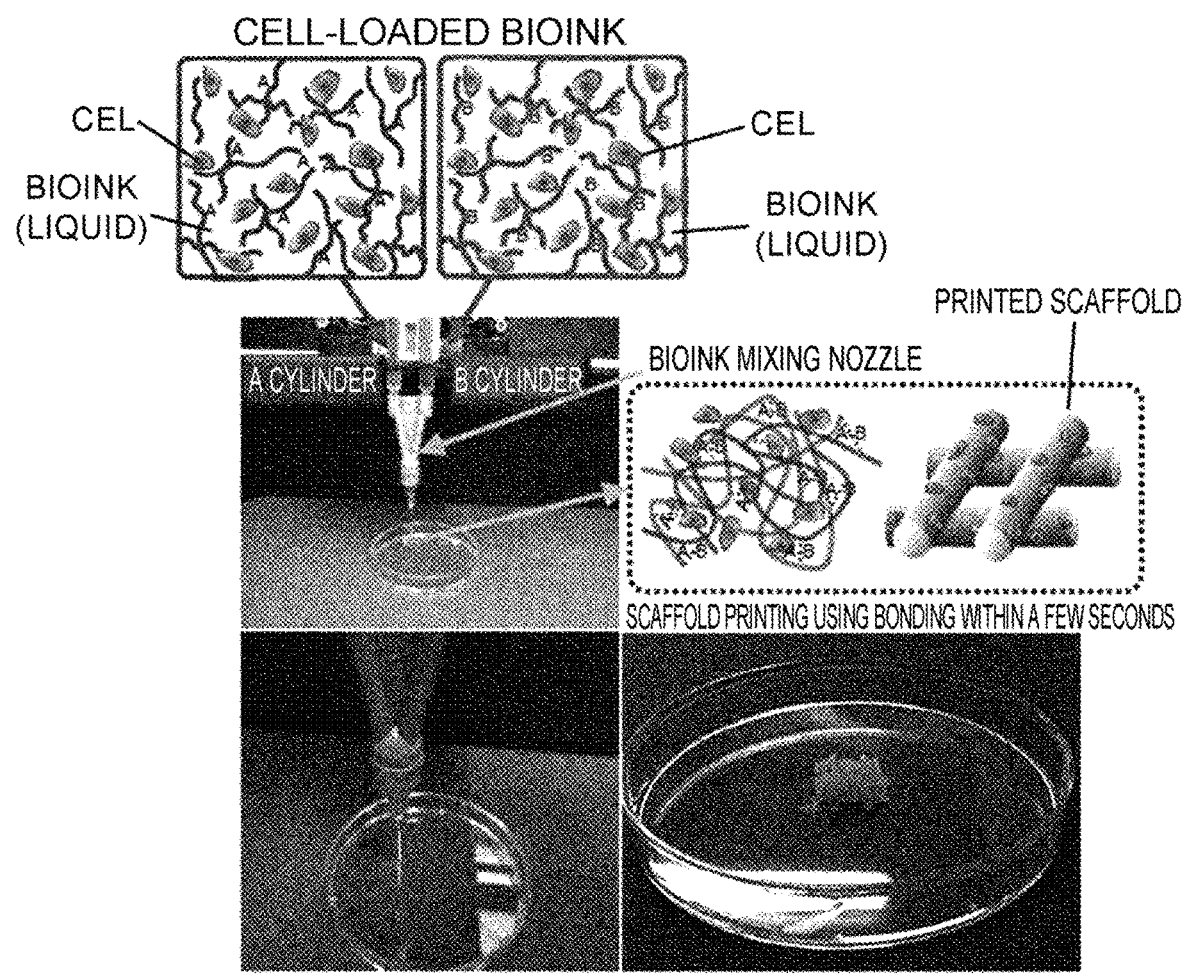
FIG. 1 is a schematic diagram illustrating printing with a two-component bioink using a 3D printer according to an exemplary embodiment of the present invention.

Hereinafter, various aspects and exemplary embodiments of the present invention will be described in further detail.

The term "biopolymer" used herein is a concept includes all polymers that can be applied to the living body due to being substantially non-toxic to a human body, being chemically inert and having no immunogenicity as well as polymers derived from a biological tissue, etc.

Two-Component Bioink

The present invention provides a two-component bioink which includes:

a first solution and a second solution separately, wherein (i) the first solution includes a first biopolymer to which a first chemical functional group is introduced and the second solution includes a second biopolymer to which a second chemical functional group able to chemically bond with the first chemical functional group is introduced; or (ii) the first solution includes a third biopolymer having a first electrostatic functional group and the second solution includes a fourth biopolymer having a second electrostatic functional group able to physically bond with the first electrostatic functional group.

First, in the two-component bioink according to the present invention, the first solution includes a first biopolymer to which a first chemical functional group is introduced, and the second solution includes a second biopolymer to which a second chemical functional group able to chemically bond with the first chemical functional group is introduced.

In the first solution, the first biopolymer has a first chemical functional group introduced thereto and may be one or more selected from the group consisting of small intestinal submucosa, hyaluronic acid, carboxymethylcellulose, alginate, chitosan, poly(N-isopropylacrylamide) and β-glycerophosphate. Here, the introduction of a first chemical functional group to the first biopolymer may be accomplished by adding a material having a first chemical functional group to the first biopolymer. Here, the first chemical functional group may be formed at a branch or end of the backbone of the first biopolymer.

Specifically, the material having a first chemical functional group may be one or more selected from the group consisting of methyltetrazine-amine, methyltetrazine-PEG4-amine, methyltetrazine-propylamine, tetrazine-PEG5-NHS ester, methyltetrazine-PEG4-NHS ester, methyltetrazine-sulfo-NHS ester, methyltetrazine-PEG4-acid, methyltetrazine-PEG12-NHS ester, methyltetrazine-NHS ester, methyltetrazine-acid, tetrazine-acid, amino-PEG4-alkyne, alkyne-PEG5-acid, alkyne-PEG-amine, oxiranylamine, 2-oxiranyl-ethylamine, acrylamide, acrylic acid and acryloyl chloride, and therefore the introduced first chemical functional group may be a tetrazine group, an alkine group, an epoxy group or an acryloyl group.

Also, in the second solution, the second biopolymer has the second chemical functional group introduced thereto, may be the same as or different from the first biopolymer, and thus be one or more selected from the group consisting of small intestinal submucosa, hyaluronic acid, carboxymethylcellulose, alginate, chitosan, poly(N-isopropylacrylamide) and β-glycerophosphate. Here, the introduction of the second chemical functional group to the second biopolymer may be accomplished by adding a material having a second chemical functional group to the second biopolymer. Here, the second chemical functional group may be formed at a branch or end of the backbone of the second biopolymer.

Specifically, the material having a second chemical functional group may be one or more selected from the group consisting of trans-cyclooctene-amine, trans-cyclooctene-NHS ester, trans-cyclooctene-PEG-NHS ester, trans-cyclooctene-PEG4-acid, azide-PEG4-amine, 3-amino-1-propanethiol, 11-mercaptoundecanoic acid, aminomethanethiol, thiol PEG amine, ethylene diamine, PEG diamine, (S)-3-amino-2-(hydroxymethyl)propionic acid and amino-acetic acid, and therefore the introduced first chemical functional group may be a tetrazine group, an alkine group, an epoxy group or an acryloyl group.

That is, a combination of the first chemical functional group and the second chemical functional group may be (tetrazine, cyclooctene), (alkyne group, azide group), (alkyne group, thiol group), (epoxy group, amine group), (epoxy group, thiol group), (acroyl group, amine group) or (acroyl group, thiol group).

The first solution and the second solution as described above may have different chemical functional groups such that when applied to a 3D printer, they can chemically bond by selective bonding between the different chemical functional groups. The chemical bonding between the first solution and the second solution takes place within a short time, particularly a few seconds and thus is very effective in solidifying the solutions.

Subsequently, in the two-component bioink according to the present invention, (ii) the first solution may include a third biopolymer having a first electrostatic functional group, and the second solution may include a fourth biopolymer having a second electrostatic functional group able to physically bond with the first electrostatic functional group.

In the first solution, the third biopolymer has a first electrostatic functional group. When the first electrostatic functional group is a cationic functional group, the third biopolymer may be one or more selected from the group consisting of chitosan and poly(N-isopropylacrylamide), and when first electrostatic functional group is an anionic functional group, the third biopolymer may be one or more selected from the group consisting of carboxymethylcellulose, hyaluronic acid and β-glycerophosphate. Here, the first electrostatic functional group may be formed at a branch or end of the backbone of the third biopolymer.

Also, in the second solution, the fourth biopolymer has a second electrostatic functional group. When the second electrostatic functional group is a cationic functional group, the fourth biopolymer may be one or more selected from the group consisting of chitosan and poly(N-isopropylacrylamide), and when the second electrostatic functional group is an anionic functional group, the fourth biopolymer may be one or more selected from the group consisting of carboxymethylcellulose, hyaluronic acid and β-glycerophosphate. Here, the second electrostatic functional group may be formed at a branch or end of the backbone of the fourth biopolymer.

That is, a combination of the first electrostatic functional group and the second electrostatic functional group may be (cationic functional group, anionic functional group) or (anionic functional group, cationic functional group).

The first solution and the second solution, as described above, may include different electrostatic functional groups such that, when applied to a 3D printer, they can form physical bonds by selective bonding between the different electrostatic functional groups. The physical bonding between the first solution and the second solution takes place within a short time and thus is very effective in solidifying the solutions.

The two-component bioink may further include, commonly in (i) and (ii), a solvent such as acetic acid, distilled water, or a buffer solution in the first solution or the second solution. Specifically, the buffer solution includes, but not limited to, one or more selected from the group consisting of 2-(n-morpholino)ethanesulfonic acid, 4-(4,6-dimethoxy-1,3,5-tiazin-2-yl)-4-methylmorpholinium chloride and phosphate buffer saline.

Also, the first solution or the second solution may further include one or more selected from the group consisting of cells, a material for preventing adhesion, a dye and a drug.

Specifically, the cells may preferably but without limitation be one or more selected from the group consisting of human-derived stem cells, muscle-derived stem cells, dental pulp stem cells, nasal concha-derived mesenchymal stromal cells, fibroblasts and smooth muscle cells. Also, when a material for preventing adhesion is further included, the 3D biomaterial may be utilized as an agent for preventing adhesion. Also, as the dye, fluorescein isothiocyanate (FITC), rhodamine, IR 780, IR 783, or propidium iodide (PI) may be used. As the drug, a generally used antibiotic, anticancer agent, inflammatory analgesic agent, antiviral agent, antibacterial agent, protein or peptide may be used, and in this regard, referring to FIG. 8, in a methotrexate (anticancer agent)-loaded tissue-engineered scaffold implemented according to an exemplary embodiment of the present invention, it can be seen that the drug is uniformly mixed and dispersed and a drug carrier containing the two-component bioink is smoothly implanted into the living body.

Two-Component Cartridge for 3D Printer

The present invention may provide a two-component cartridge for a 3D printer or a 3D printer which contains the two-component bioink.

The detailed description of the two-component bioink has been provided above.

3D Biomaterial and Method for Preparing the Same

The present invention provides a 3D biomaterial formed by chemically or physically combining the two-component bioink.

The 3D biomaterial is formed from a two-component bioink composed of a biocompatible composition and may be a tissue-engineered scaffold, a drug carrier or an anti-adhesive agent.

The detailed description of the two-component bioink has been provided above.

Also, the present invention provides a method for preparing a 3D biomaterial, including:

(a-1) preparing a first solution by adding a material having a first chemical functional group to a first biopolymer; (b-1) preparing a second solution by adding a material having a second chemical functional group enabled to chemically bond with a first chemical functional group to a second biopolymer; and (c-1) chemically combining the first solution with the second solution, or (a-2) preparing a first solution having a third biopolymer having a first electrostatic functional group; (b-2) preparing a second solution having a fourth biopolymer having a second electrostatic functional group; and (c-2) physically combining the first solution with the second solution.

First, the method for preparing a 3D biomaterial according to the present invention may include: (a-1) preparing a first solution by adding a material having a first chemical functional group to a first biopolymer; (b-1) preparing a second solution by adding a material having a second chemical functional group able to chemically bond with a first chemical functional group to a second biopolymer; and (c-1) chemically combining the first solution with the second solution.

The detailed descriptions of the first biopolymer, the first chemical functional group, the first solution, the second biopolymer, the second chemical functional group and the second solution have been provided above.

Specifically, a molar ratio of the first biopolymer and the material having a first chemical functional group in (a-1) or a molar ratio of the second biopolymer and the material having a second chemical functional group in (b-1) may be in a range from 1:400 to 1:600, but the present invention is not limited thereto. Here, when the molar ratio of the biopolymer and the material having a chemical functional group is less than 1:400, mechanical strength is decreased, but when the molar ratio of the biopolymer and the material having a chemical functional group is more than 1:600, mechanical strength is excessively increased, and thus transfers of various materials are limited by an excessive degree of crosslinking.

Specifically, the material having a first chemical functional group in (a-1) is a material for introducing a first chemical functional group to the first biopolymer and may be one or more selected from the group consisting of methyltetrazine-amine, methyltetrazine-PEG4-amine, methyltetrazine-propylamine, tetrazine-PEG5-NHS ester, methyltetrazine-PEG4-NHS ester, methyltetrazine-sulfo-NHS ester, methyltetrazine-PEG4-acid, methyltetrazine-PEG12-NHS ester, methyltetrazine-NHS ester, methyltetrazine-acid or tetrazine-acid for introducing tetrazine; amino-PEG4-alkyne, alkyne-PEG5-acid or alkyne-PEG-amine for introducing an alkyne group; oxiranylamine or 2-oxiranyl-ethylamine for introducing an epoxy group; and acrylamide, acrylic acid or acryloyl chloride for introducing an acryloyl group.

Also, the material having a second chemical functional group in (b-1) may be one or more selected from the group consisting of trans-cyclooctene-amine, trans-cyclooctene-NHS ester, trans cyclooctene-PEG-NHS ester or trans cyclooctene-PEG4-acid for introducing cyclooctene; azide-PEG4-amine for introducing an azide group; 3-amino-1-propanethiol, 11-mercaptoundecanoic acid or amino-methanethiol for introducing a thiol group; thiol PEG amine for introducing a thiol group or amine group; and ethylene diamine, PEG diamine, (S)-3-amino-2-(hydroxymethyl)propionic acid or amino-acetic acid for introducing an amine group.

Meanwhile, the content of the first biopolymer in the first solution in (a-1) or the content of the second biopolymer in the second solution in (b-1) may be in a range from 1 wt % to 30 wt %, but the present invention is not limited thereto. Here, when the content of the biopolymer is outside the above range, the biopolymer may not be usable as a bioink due to high viscosity.

Subsequently, the method for preparing a 3D biomaterial according to the present invention may include: (a-2) preparing a first solution having a third biopolymer having a first electrostatic functional group; (b-2) preparing a second solution having a fourth biopolymer having a second electrostatic functional group; and (c-2) physically combining the first solution with the second solution.

The detailed descriptions of the third biopolymer, the first electrostatic functional group, the first solution, the fourth biopolymer, the second electrostatic functional group and the second solution have been provided above.

Specifically, the content of the third biopolymer in the first solution in (a-2) or a content of the fourth biopolymer in the second solution in (b-2) may be in a range from 1 wt % to 30 wt %, but the present invention is not limited thereto. Here, when the content of the biopolymer is outside the above range, the biopolymer may not be usable as a bioink due to high viscosity.

Hereinafter, the present invention will be described in further detail with reference to examples, but the scope of the present invention will not be construed as being diminished or limited by the examples, etc. below. Also, based on the descriptions disclosed in the present invention including the following examples, it is obvious that the present invention without specifically presented experimental results can be easily implemented by those of ordinary skill in the art, and it is also obvious that such alternation and modification are included in the accompanying claims.

Also, experimental results presented below only demonstrate representative experimental results of the above examples and comparative examples, and each effect of various exemplary embodiments of the present invention not explicitly presented below will be specifically described in corresponding sections.

Preparation Example 1

With respect to a total weight of the entire solution, 1 wt % of small intestinal submucosa powder, 0.1 wt % of pepsin and 3 wt % of acetic acid were added, a resulting mixture was stirred for 48 hours to react, an 1 N sodium hydroxide solution was added to reach a pH value of 7.4 for the entire solution, thereby preparing a small intestinal submucosa solution.

Preparation Examples 2 to 4

Hyaluronic acid, carboxymethylcellulose powder, and alginate were each added to deionized water, stirred at room temperature for 12 hours, thereby preparing a hyaluronic acid solution, a carboxymethylcellulose solution and an alginate solution (however, the content of each component is listed in Table 1 below).

TABLE 1

| Component (wt %) | Preparation Example2 | Preparation Example3 | Preparation Example4 |
| --- | --- | --- | --- |
| Hyaluronic acid | 1 | — | — |
| Carboxymethyl-cellulose | — | 8 | — |
| Alginate | — | — | 1 |
| Deionized water | 99 | 92 | 99 |

Examples 1 to 7

1. Preparation of First Solution
After 97.6 mg of 100 mM 2-(N-morpholino)ethanesulfonic acid and 3.5 g of 2.5M 4-(4,6-Dimethoxy-1,3,5-triazin-2yl)-4-methylmorpholinium chloride were added to the solution of Preparation Example 1, the solution and a material having a first chemical functional group were added to achieve a molar ratio of 1:500, stirred for 72 hours to react, dialyzed for 72 hours, cooled at −80° C. and freeze-dried, thereby preparing a chemical functional group-introduced first solution.

2. Preparation of Second Solution

A chemical functional group-introduced second solution was prepared as described above, except that a material having a second chemical functional group instead of the first chemical functional group was added.

However, specific types of the materials containing the first and second chemical functional groups are listed in Table 2 below.

TABLE 2

| Type | Material having first chemical functional group | Material having second chemical functional group |
|---|---|---|
| Example 1 | methyltetrazine-PEG4-amine | trans-cyclooctene-amine |
| Example 2 | amino-PEG4-alkyne | azide-PEG4-amine |
| Example 3 | amino-PEG4-alkyne | thiol-PEG-amine |
| Example 4 | 2-oxiranyl-ethylamine | PEG diamine |
| Example 5 | 2-oxiranyl-ethylamine | thiol-PEG-amine |
| Example 6 | acrylamide | PEG diamine |
| Example 7 | acrylamide | thiol-PEG-amine |

Examples 8 to 14

Processes were performed as described in Examples 1 to 7, except that the solution of Preparation Example 2 was used instead of the solution of Preparation Example 1.

Examples 15 to 21

Processes were performed as described in Examples 1 to 7, except that the solution of Preparation Example 3 was used instead of the solution of Preparation Example 1.

Examples 22 to 28

Processes were performed as described in Examples 1 to 7, except that the solution of Preparation Example 4 was used instead of the solution of Preparation Example 1.

Examples 29 to 33

A two-component bioink was prepared as described in Example 1, except further including stem cells or somatic cells being included in both of a first solution and a second solution at a concentration of $1 \times 10^6$ cells/ml (however, a specific type of the added stem cells or somatic cells is listed in Table 3 below).

TABLE 3

| | Example | | | | |
|---|---|---|---|---|---|
| | Example 29 | Example 30 | Example 31 | Example 32 | Example 33 |
| Type of cells | Bone marrow-derived stem cells (hBMSC) | Muscle-derived stem cells (hMDSC) | Dental pulp stem cells (hDPSC) | Fibroblast | Smooth muscle cells (SMC) |

Example 34

A two-component bioink was prepared as described in Example 1, except further including FITC-introduced methotrexate being loaded in both of a first solution and a second solution at a concentration of 375 μg/ml.

Example 35

A two-component bioink was prepared as described in Example 1, except further including IR-780 iodide dye being introduced to both of a first solution and a second solution at a concentration of 317 μg/ml.

Example 36

1. Preparation of First Solution

An electrostatic functional group-introduced first solution was prepared by preparing a chitosan solution by adding 2.5 wt % of chitosan powder to 0.1 N acetic acid with respect to the total weight of the solution and stirring the mixture at room temperature for 12 hours, and then by stabilizing the prepared chitosan solution at 4° C. for 48 hours.

2. Preparation of Second Solution

An electrostatic functional group-introduced second solution was prepared by adding 12 wt % of carboxymethylcellulose powder to 12 wt % of phosphate buffer saline with respect to the total weight of the solution, stirring the mixture, and stabilizing the resulting mixture at 4° C. for 48 hours.

Example 37

1. Preparation of First Solution

A process was performed as described in Example 36.

2. Preparation of Second Solution

A process was performed as described in Example 36 except that 3 wt % of hyaluronic acid powder was added instead of carboxymethylcellulose powder.

Example 38

1. Preparation of First Solution

A process was performed as described in Example 36.

2. Preparation of Second Solution

A second solution was prepared by preparing a solution by adding 5 wt % of β-glycerophosphate powder to phosphate buffer saline with respect to the total weight of the solution, stirring the mixture, then stabilizing the mixture at 4° C. for 48 hours, and mixing the stabilized mixture with a carboxymethylcellulose solution prepared as described in Example 12.

Example 39

1. Preparation of First Solution

A first solution was prepared by adding 20 wt % of poly(N-isopropylacrylamide) to phosphate buffer saline, stirring the mixture, and then stabilizing the mixture at 4° C. for 48 hours.

2. Preparation of Second Solution

A process was performed as described in Example 36.

Examples 40 to 43

A two-component bioink was prepared as described in Example 36, except further including PKH-labeled cells being included in both of a first solution and a second solution at a concentration of $1 \times 10^6$ cells/ml (however, a specific type of the added cells is listed in Table 4 below).

TABLE 4

| Examples | Example 40 | Example 41 | Example 42 | Example 43 |
|---|---|---|---|---|
| Type of cells | Bone marrow-derived stem cells (hBMSC) | Muscle-derived stem cells (hMDSC) | Nasal concha-derived mesenchymal stromal cells (hTMSC) | Dental pulp stem cells (hDPSC) |

Example 44

A two-component bioink was prepared as described in Example 36, except further including 1 mg/μl of curcumin being added to both of a first solution and a second solution.

Example 45

A process was performed as described in Example 44, except that curcumin-loaded PLGA microparticles prepared using a uniaxial ultrasonic nozzle method was added.

Examples 46 and 47

A process was performed as described in Example 36, except further including 3 mg of NIR-783 dye or Rhodamine dye being mixed to react for 24 hours and being removed unreacted dye using a dialysis membrane for 2 days.

Experimental Example 1: Preparation of Tissue-Engineered Scaffold

Figure 2:
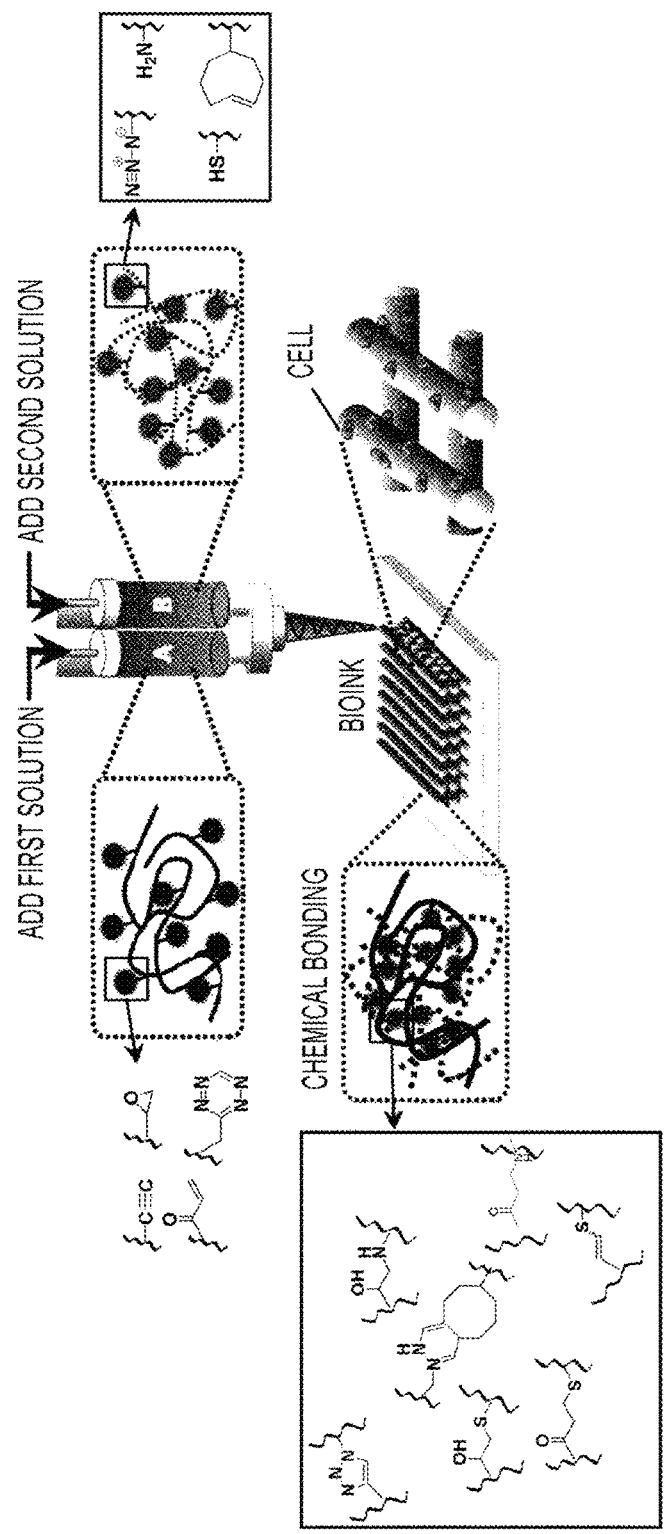
FIG. 2 is a schematic diagram demonstrating printing with a two-component bioink utilizing chemical bonding using a 3D printer according to Examples 1 to 4.

As shown in FIG. 2, using a 3D printer having two cylinders, a tissue-engineered scaffold was prepared from a 3D biomaterial by extruding a first solution added to a cylinder A and a second solution added to a cylinder B.

Figure 3:
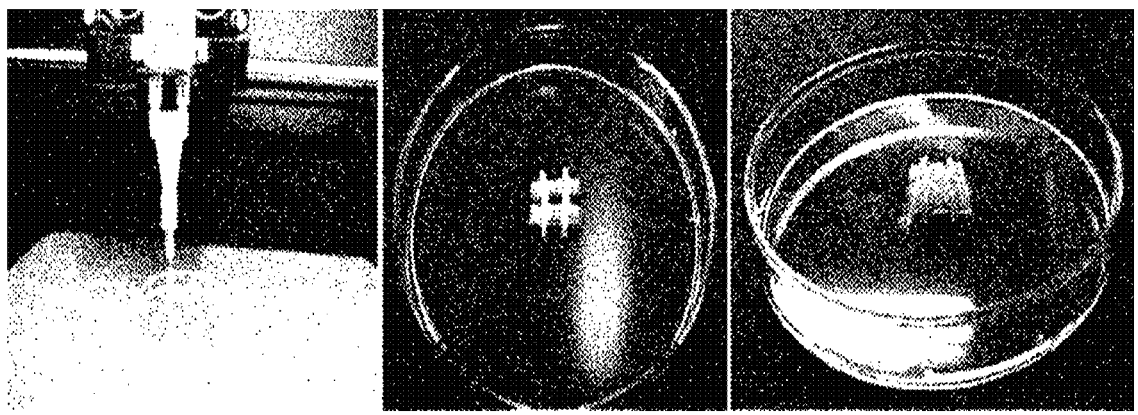
FIG. 3 shows an image of a tissue-engineered scaffold printed with the two-component bioink of Example 1 using a 3D printer.
Figure 4:
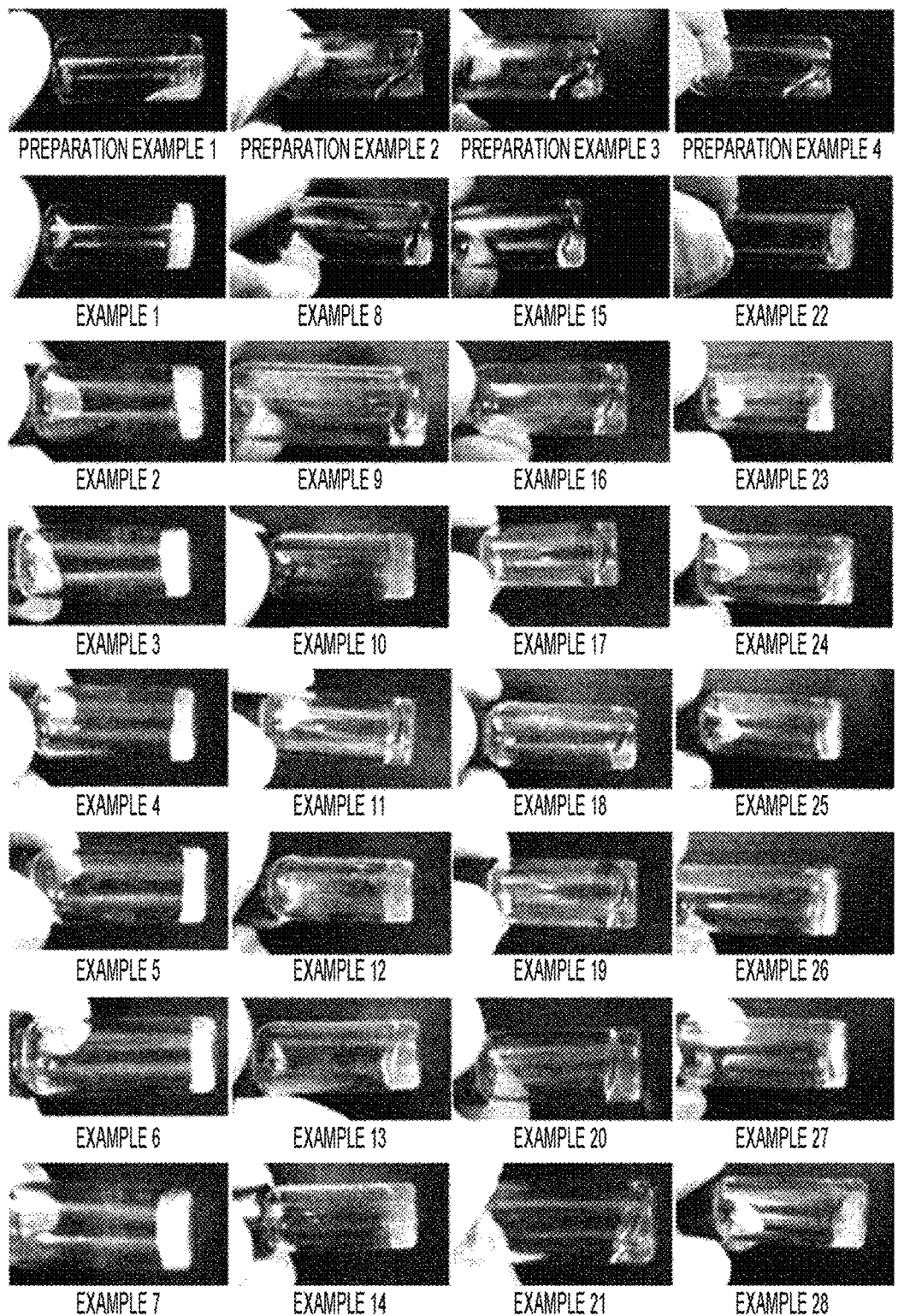
FIG. 4 shows images of two-component bioinks of Examples 1 to 28.

FIG. 3 shows a result of printing with the two-component bioink of Example 1, and a tissue-engineered scaffold prepared with a solid 3D biomaterial could also be seen with the naked eye.

Experimental Example 2: Evaluation of Cell Viability

Figure 5:
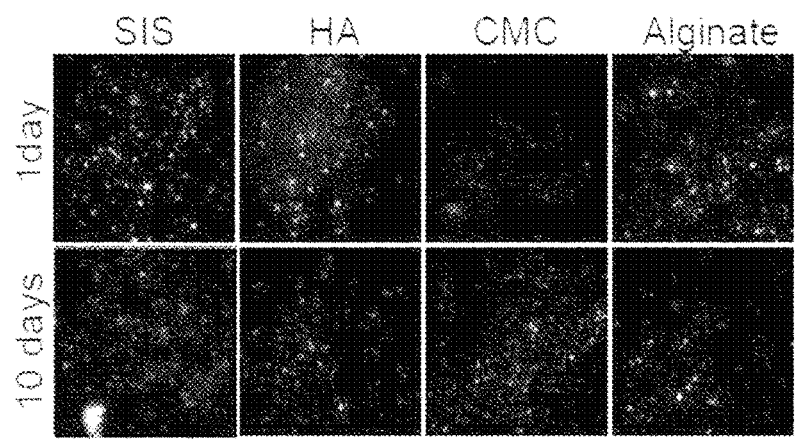
FIG. 5 shows images where tissue-engineered scaffolds printed using a 3D printer with two-component bioinks of Examples 1 (SIS), 8 (HA), 15 (CMC) and 22 (Alginate) mixed with cells are grown for 10 days and then the cells in the tissue-engineered scaffolds are observed using a fluorescence microscope.
Figure 6:
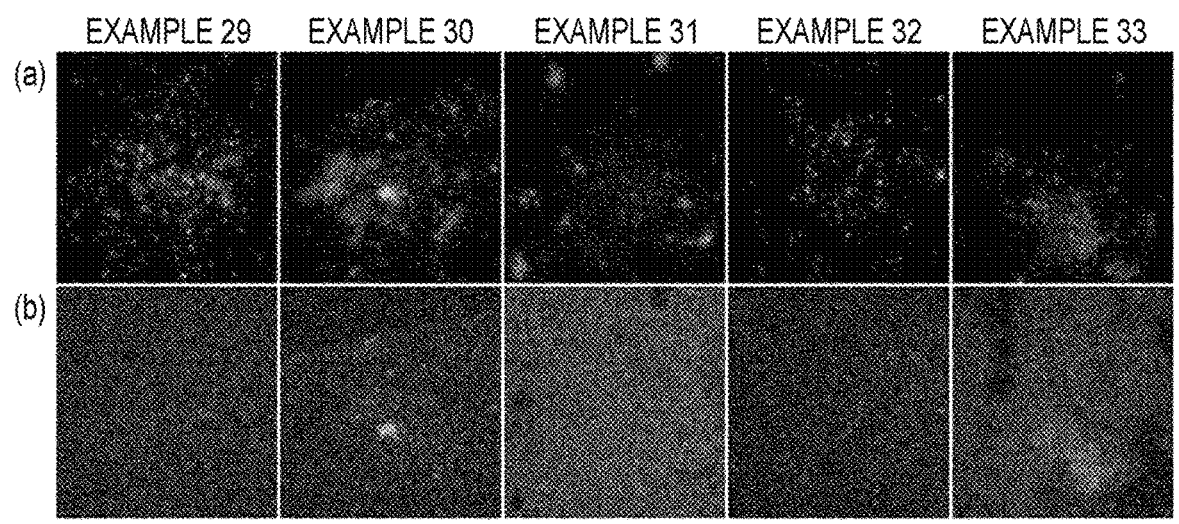
FIG. 6(a) shows fluorescence microscopic images of a surface of tissue-engineered scaffolds printed with two-component bioinks of Examples 29 to 33 using a 3D printer.
FIG. 6(b) is a combination of a phase difference image and a fluorescent image.

Tissue-engineered scaffolds that are 3D biomaterials printed with two-component bioinks of Example 1, 8, 15 and 22 using a 3D printer were cultured for 10 days, then cell viability and behaviors were observed using a fluorescent microscope, and the results are shown in FIG. 5.

Referring to FIG. 5, it can be seen that cells were evenly distributed and survived even after 10 days.

Experimental Example 3: Evaluation of Biocompatibility

Figure 7:
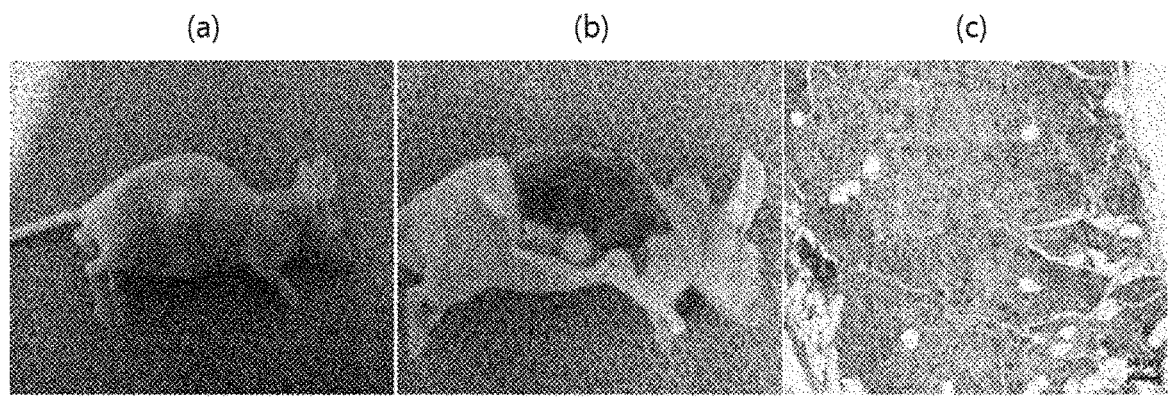
FIG. 7(a) shows a nude mouse into which a tissue-engineered scaffold printed with the two-component bioink of Example 1 using a 3D printer is implanted.
FIG. 7(b) shows extraction of the implanted scaffold.
FIG. 7(c) is an H&E image of the extracted scaffold.

To evaluate biocompatibility of a tissue-engineered scaffold as a 3D biomaterial printed with the two-component bioink of Example 1 using a 3D printer, the scaffold was implanted into a subcutaneous area of a nude mouse, and the implanted area was extracted several days later and subjected to hematocylin and eosin (H&E) staining, and the evaluation result is shown in FIG. 7.

Referring to FIG. 7, since necrosis of tissue around the scaffold-implanted area or cell death is not observed, it can be identified that the scaffold was grown in a biocompatible format. Also, it can be seen that cells or tissue of a recipient are included in the scaffold, and it can be identified that the scaffold is effectively biocompatible.

Experimental Example 4: Evaluation of Suitability of Composition as Drug Carrier Using Chemical Bonding A tissue-engineered scaffold prepared as a 3D biomaterial printed with the two-component bioink of Example 34 using a 3D printer was implanted into a subcutaneous area of a nude mouse, after 24 hours of the implantation, the scaffold was observed by FOBI, and the result is shown in FIG. 8.

Figure 8:
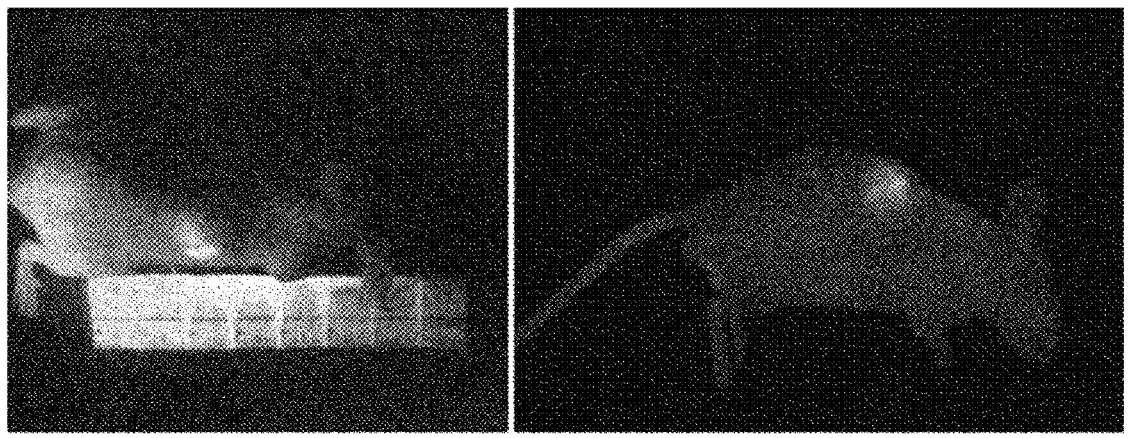
FIG. 8 shows in vivo images of a tissue-engineered scaffold printed with a two-component bioink of Example 34 using a 3D printer and implanted into a nude mouse as obtained by fluorescence-labeled organism bioimaging (FOBI).

Referring to FIG. 8, it can be seen that after 24 hours, the introduced drug is well maintained in the scaffold.

Experimental Example 5: Evaluation of In Vivo Image Tracking Possibility

Figure 9:
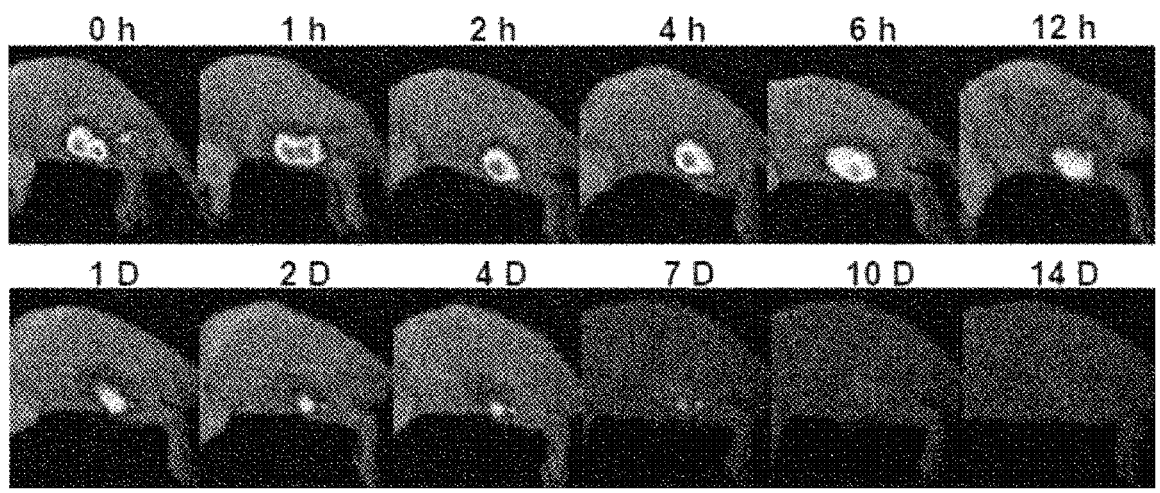
FIG. 9 shows in vivo images of a tissue-engineered scaffold printed with the two-component bioink of Example 35 using a 3D printer and implanted into a nude mouse as obtained by FOBI over time.
Figure 10:
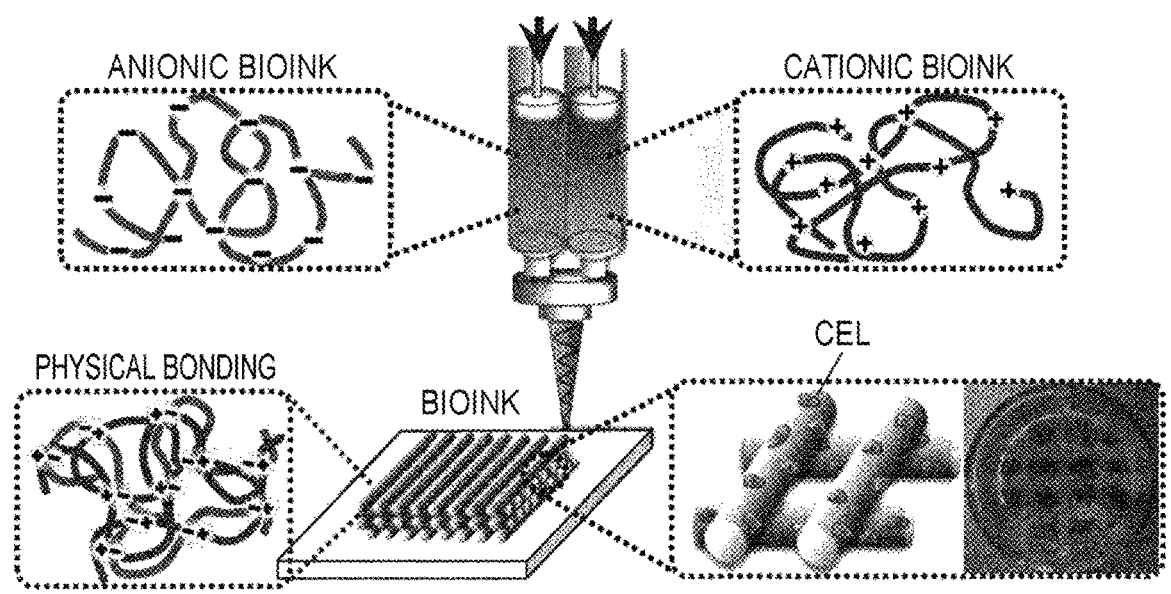
FIG. 10 is a schematic diagram illustrating a printing process with a two-component bioink utilizing an electrostatic interaction using a 3D printer according to Examples 36 to 39.
Figure 18:
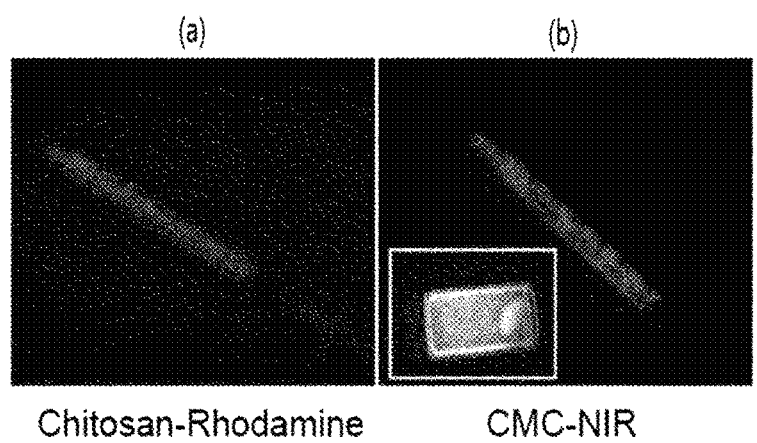
FIG. 18 is a fluorescent image obtained by FOBI according to Examples 46 and 47.

Scaffolds printed with in vivo trackable dye-loaded two-component bioinks of Example 35, 46 and 47 using a 3D printer were implanted into the body of nude mice and observed using FOBI which is an imaging device, and the results are shown in FIGS. 9 and 18.

Referring to FIGS. 9 and 18, it can be confirmed that image tracking is possible not only right after the implantation of the scaffolds prepared with the two-component bioinks of Example 35, 46 and 47 but, even after 14 days in the case of Example 35.

Experimental Example 6: Evaluation of Lattice-Shaped Printing Possibility

Figure 11:
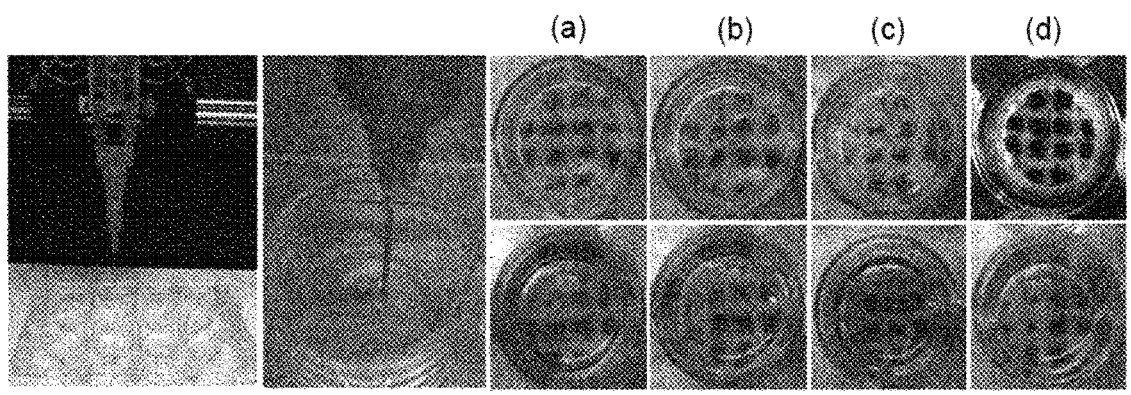
FIG. 11 is an image of the result of 3D printing with the two-component bioink of Example 36 in a lattice shape into a 12-well plate, where

As shown in FIG. 11, printing with the two-component bioinks of Examples 36 to 39 was performed in a lattice shape into a 12-well plate, and the results are shown in FIGS. 11(a) to (d).

Referring to the upper panels of FIGS. 11(a) to (d), it can be seen that printing is well accomplished in a desired lattice shape, and the lattice shape is well maintained even after cell culture media were added as shown in the lower panels. Therefore, it can be confirmed that when printing is performed with cell-loaded bioink and then a cell culture medium is added, the scaffold is well maintained without disintegrating.

Experimental Example 7: Evaluation of Toxicity

Figure 12:
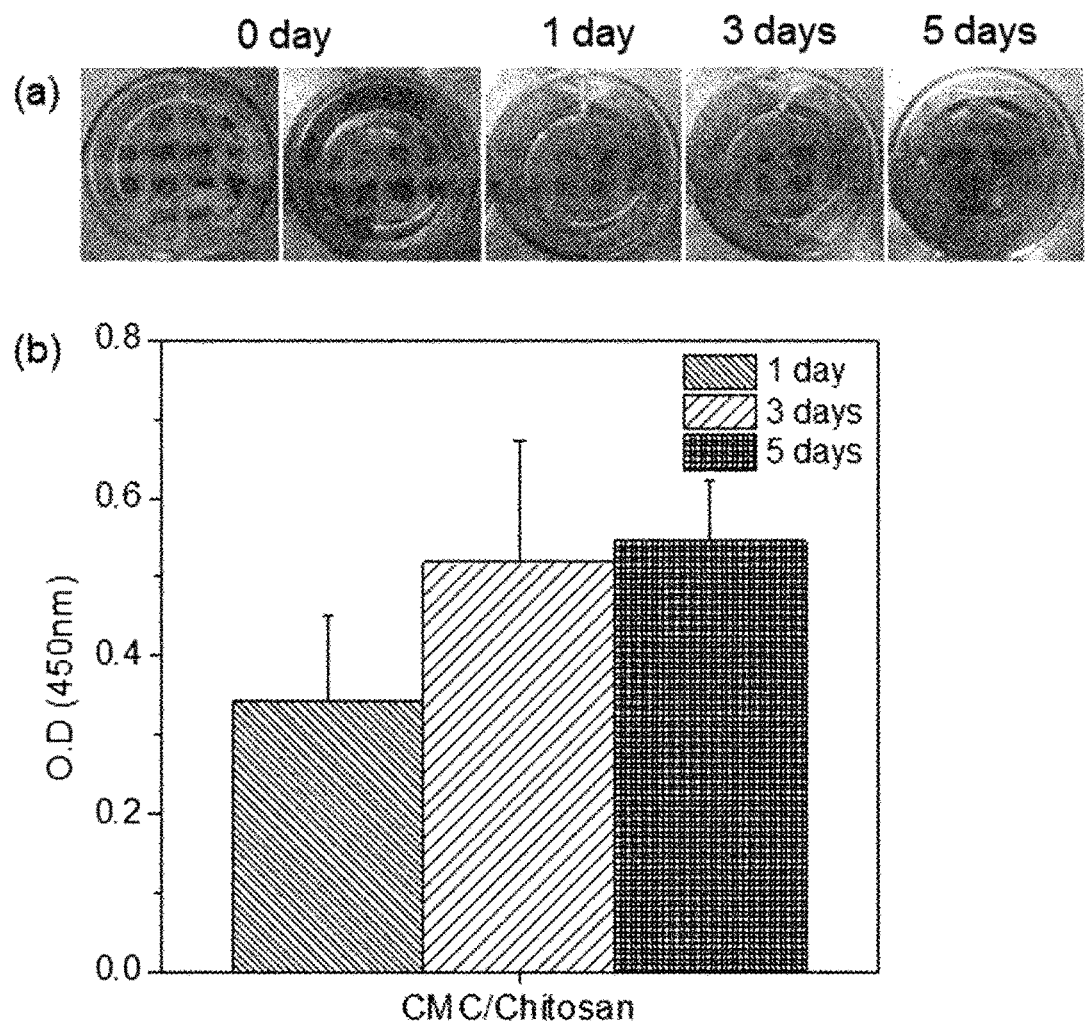
FIG. 12(a) is an image of the output of printing with the two-component bioink of Example 41 in a lattice shape into a 12-well plate.
FIG. 12(b) is a graph showing the toxicity evaluation result for Example 41.

After printing was performed with the two-component bioink of Example 41 in a lattice shape as described in Experimental Example 6, a WST-1 cell proliferation assay kit was added after 1, 3 and 5 days from starting cell culture to evaluate toxicity, and the result is shown in FIG. 12.

Figure 13:
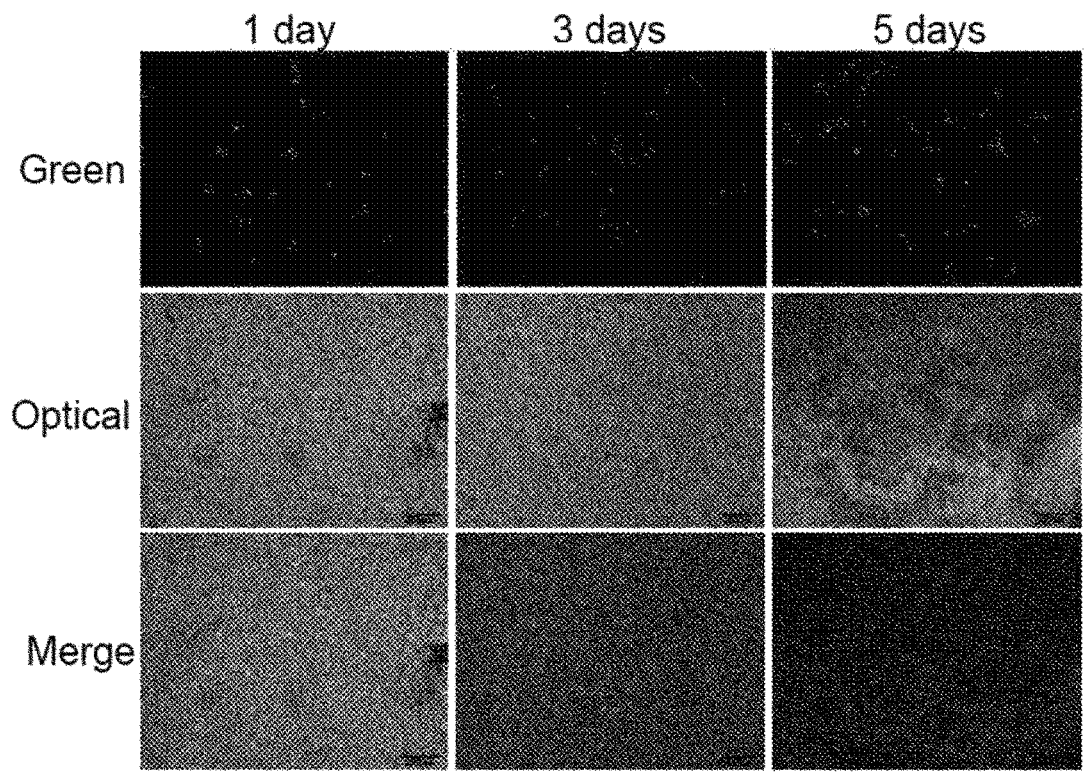
FIG. 13 is a fluorescent image of a tissue-engineered scaffold printed with the two-component bioink of Example 41 using a 3D printer as obtained using a fluorescence microscope.
Figure 14:
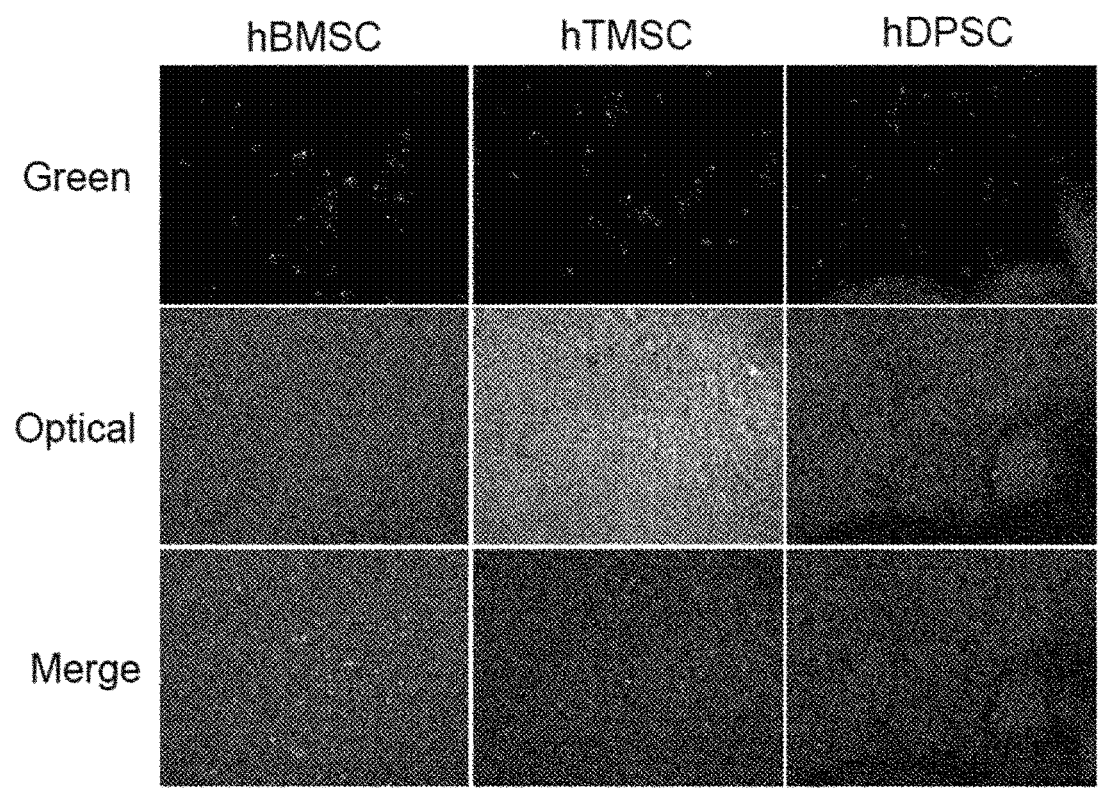
FIG. 14 shows fluorescent images of tissue-engineered scaffolds printed with the two-component bioinks of Examples 40, 42 and 43 using a 3D printer as obtained using a fluorescence microscope.
Figure 15:
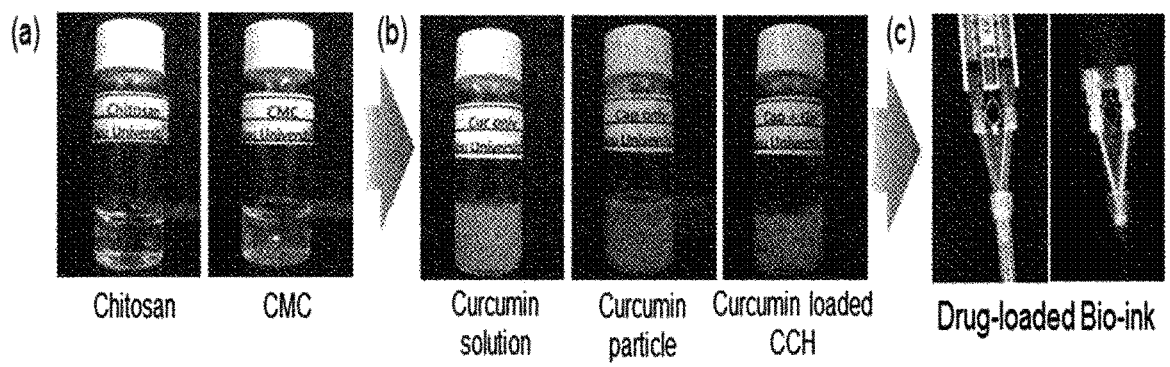
FIG. 15(a) shows a cationic or anionic solution of Example 36.
FIG. 15(b) shows a solution in which curcumin (Cur) is suspended in phosphate buffer saline and a solution in which curcumin-loaded microparticles are suspended in phosphate buffer saline, and a cationic or anionic mixed solution of Example 44.
FIG. 15(c) shows a cylinder injected with a drug-loaded bioink.

Also, the morphology and behavior of the cells of the scaffolds printed with the two-component bioinks of Examples 40 to 43 were observed, and the results are shown in FIGS. 13 and 14.

Referring to FIGS. 13 and 14, it can be seen that the cells were well distributed and survived in the scaffolds even after 5 days.

Figure 16:
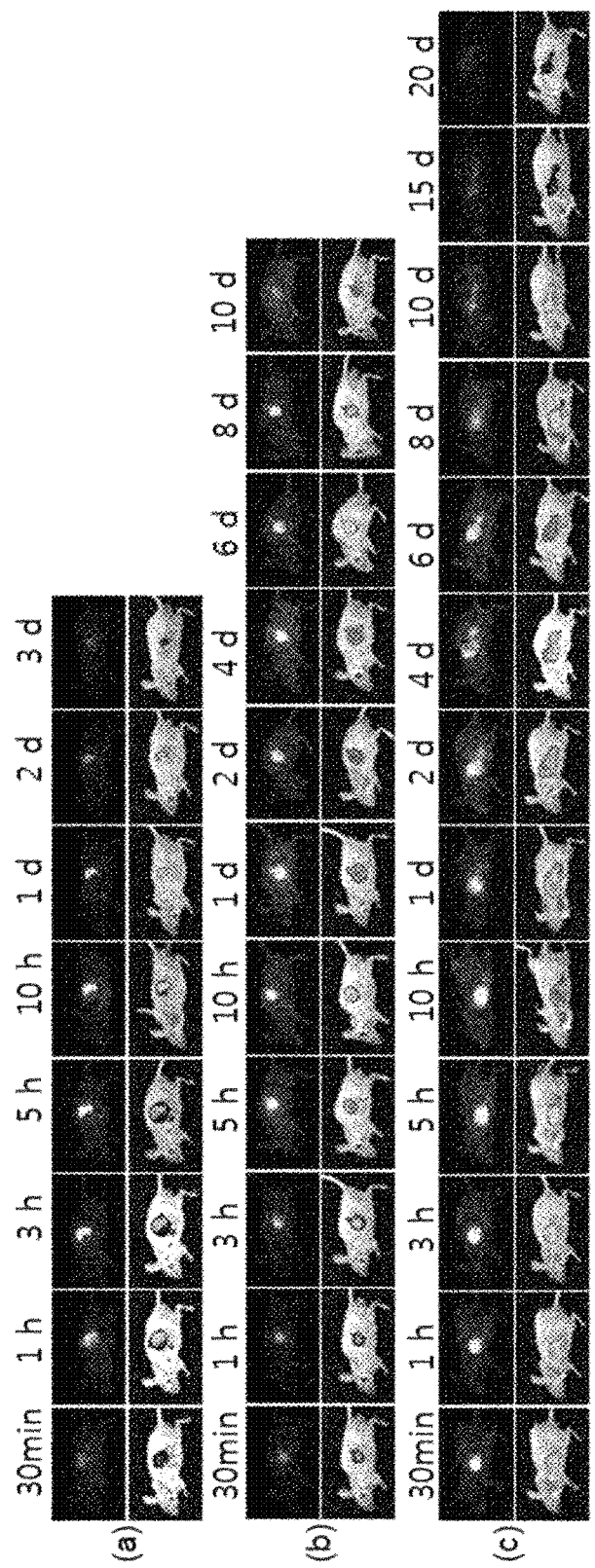
FIG. 16(a) shows a curcumin-injected nude mouse.
FIG. 16(b) shows a nude mouse injected with curcumin-loaded microparticles.
FIG. 16(c) shows curcumin being released over time in Example 44.
Figure 17:
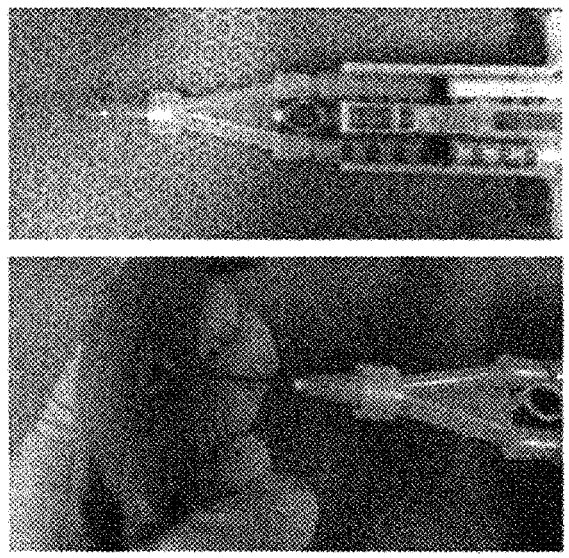
FIG. 17(a) shows a direct injection of a two-component bioink of Example 45 into a nude mouse.
FIG. 17(b) shows a graph of comparative anticancer effects of Example 45 and comparative examples on nude mice of an A-253 cell-injected tumor model (Cur-M: curcumin-loaded microparticles, Cur-M-loaded CCH: bioink in which curcumin-loaded microparticles are mixed with chitosan/carboxymethylcellulose, repeat free Cur injection: repeated injection of curcumin, single free Cur injection: single injection of curcumin in the early stage, and saline: injection of saline).
Figure 17:
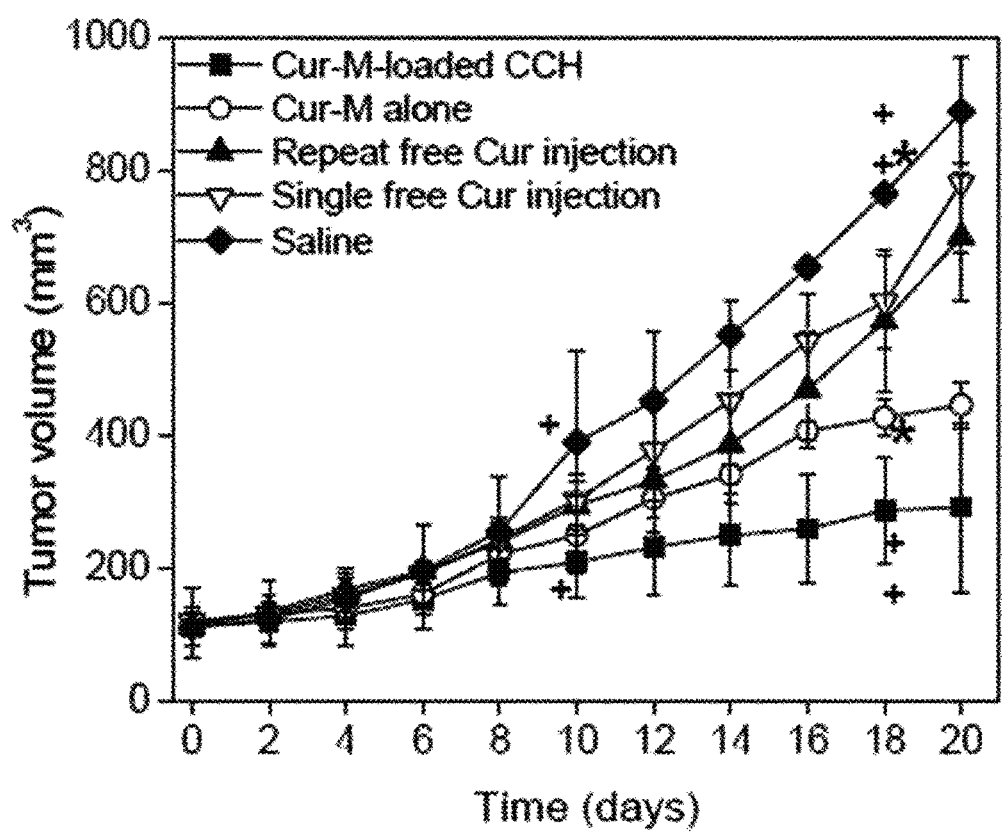

Experimental Example 8: Evaluation of Suitability of Composition as Drug Carrier Using Electrostatic Attraction The scaffolds printed with the two-component bioinks of Examples 44 and 45 were implanted into a subcutaneous area of nude mice and observed by FOBI over time, and the results are shown in FIGS. 16 and 17 (however, as a comparative example, a tumor model was prepared by injecting A-253 cells into a nude mouse).

FIG. 16(a) shows a nude mouse to which curcumin was injected, FIG. 16(b) shows a nude mouse to which curcumin-loaded microparticles were injected, and FIG. 16(c) shows a nude mouse in which curcumin of Example 44 was released. It can be confirmed that the drug-loaded Example 44 was increased within the duration of in vivo drug sustainment, and thus bioavailability was increased. Also, referring to FIG. 17, it can be confirmed that Example 45 exhibits increased drug efficacy and thus an excellent anti-cancer effect.

Therefore, the two-component bioinks according to various exemplary embodiments of the present invention are biocompatible liquid compositions which have chemical bonding or physical bonding by an electrostatic attraction, are applied to a 3D printer, and exhibit excellent effectiveness in providing a solid 3D biomaterial.

Also, by adding cells, a material for preventing adhesion, a dye, a drug, etc. to the two-component bioink, the two-component bioink can be applied to various fields including 3D biomaterials including a tissue-engineered scaffold, a drug carrier and an anti-adhesive agent, etc.

The invention claimed is:

1. A two-component bioink for 3D printing, comprising: a first solution and a second solution separately,
wherein the first solution includes a first biopolymer having a first chemical functional group, and the second solution includes a second biopolymer having a second chemical functional group able to chemically bond with the first chemical functional group,
wherein a combination of the first chemical functional group and the second chemical functional group is tetrazine and cyclooctene, alkyne group and azide group, alkyne group and thiol group, epoxy group and amine group, epoxy group and thiol group, acroyl group and amine group, or acroyl group and thiol group, and
wherein the first chemical functional group is introduced to the first biopolymer from one or more of the material selected from the group consisting of methyltetrazine-amine, methyltetrazine-PEG4-amine, methyltetrazine-propylamine, tetrazine-PEG5-NHS ester, methyltetrazine-PEG4-NHS ester, methyltetrazine-sulfo-NHS ester, methyltetrazine-PEG4-acid, methyltetrazine-PEG12-NHS ester, methyltetrazine-NHS ester, methyltetrazine-acid, tetrazine-acid, amino-PEG4-alkyne, alkyne-PEG5-acid, alkyne-PEG-amine, oxiranylamine, 2-oxiranyl-ethylamine, acrylamide, acrylic acid and acryloyl chloride, and
the second chemical functional group is introduced to the second biopolymer from one or more of the material selected from the group consisting of trans-cyclooctene-amine, trans-cyclooctene-NHS ester, trans-cyclooctene-PEG-NHS ester, trans-cyclooctene-PEG4-acid, azide-PEG4-amine, 3-amino-1-propanethiol, 11-mercaptoundecanoic acid, amino-methanethiol, thiol PEG amine, ethylene diamine, PEG diamine, (S)-3-amino-2-(hydroxymethyl)propionic acid and amino-acetic acid.

2. The bioink of claim 1, wherein the first solution or second solution further includes one or more selected from the group consisting of cells, a material for preventing adhesion, a dye and a drug.

3. The bioink of claim 2, wherein the cells are one or more selected from the group consisting of human-derived stem cells, muscle-derived stem cells, dental pulp stem cells, nasal concha-derived mesenchymal stromal cells, fibroblasts and smooth muscle cells.

4. A 3D biomaterial comprising the two-component bioink of claim 1, wherein the first and second biopolymers are chemically combined by the combination of the first chemical functional group and the second chemical functional group.

5. The 3D biomaterial of claim 4, which is a tissue-engineered scaffold, a drug carrier or an anti-adhesive agent.

6. A method for preparing a 3D biomaterial, comprising:
(a) preparing a first solution by adding a material having a first chemical functional group to a first biopolymer;
(b) preparing a second solution by adding a material having a second chemical functional group able to chemically bond with a first chemical functional group to a second biopolymer; and (c) chemically combining the first solution with the second solution, and
wherein the material having a first chemical functional group in (a) is one or more selected from the group consisting of methyltetrazine-amine, methyltetrazine-PEG4-amine, methyltetrazine-propylamine, tetrazine-PEG5-NHS ester, methyltetrazine-PEG4-NHS ester, methyltetrazine-sulfo-NHS ester, methyltetrazine-PEG4-acid, methyltetrazine-PEG12-NHS ester, methyltetrazine-NHS ester, methyltetrazine-acid, tetrazine-acid, amino-PEG4-alkyne, alkyne-PEG5-acid, alkyne-PEG-amine, oxiranylamine, 2-oxiranyl-ethylamine, acrylamide, acrylic acid and acryloyl chloride, and
wherein the material having a second chemical functional group in (b) is one or more selected from the group consisting of trans-cyclooctene-amine, trans-cyclooctene-NHS ester, trans-cyclooctene-PEG-NHS ester, trans-cyclooctene-PEG4-acid, azide-PEG4-amine, 3-amino-1-propanethiol, 11-mercaptoundecanoic acid, amino-methanethiol, thiol PEG amine, ethylene diamine, PEG diamine, (S)-3-amino-2-(hydroxymethyl)propionic acid and amino-acetic acid.

7. The method of claim 6, wherein a molar ratio of the first biopolymer and the material having a first chemical functional group in (a) or a molar ratio of the second biopolymer and the material having a second chemical functional group in (b) is 1:400 to 1:600.

8. The method of claim 6, wherein the content of the first biopolymer in the first solution in (a) or the content of the second biopolymer in the second solution in (b) is 1 wt % to 30 wt %.

\* \* \* \* \*